United States Patent [19]

Yu et al.

[11] Patent Number: 6,051,609
[45] Date of Patent: Apr. 18, 2000

[54] ADDITIVES ENHANCING THE EFFECT OF THERAPEUTIC AGENTS

[75] Inventors: Ruey J. Yu, Ambler; Eugene J. Van Scott, Rydal, both of Pa.

[73] Assignee: Tristrata Technology, Inc., Wilmington, Del.

[21] Appl. No.: 09/222,997

[22] Filed: Dec. 30, 1998

Related U.S. Application Data

[63] Continuation of application No. 08/926,030, Sep. 9, 1997, Pat. No. 5,962,526.

[51] Int. Cl.⁷ ....................................................... A61K 7/00
[52] U.S. Cl. .......................... 514/557; 514/574; 514/844; 514/847; 514/873
[58] Field of Search ..................................... 514/557, 574, 514/844, 847, 873

[56] References Cited

U.S. PATENT DOCUMENTS 5,091,171  2/1992  Yu et al. .................................. 424/642

*Primary Examiner*—Michael A. Williamson
*Attorney, Agent, or Firm*—Foley & Lardner

[57] ABSTRACT

Composition and method for enhancing therapeutic effects of topically applied agents are disclosed. The cosmetic or therapeutic composition may include one or more of cosmetic or pharmaceutical agents present in a total amount of from 0.01 to 40 percent and one or more of hydroxycarboxylic acids or related compounds present in a total amount of from 0.01 to 99 percent by weight of the total composition. The cosmetic and pharmaceutical agents may include but not limited to age spots, wrinkles and keratoses removing agents; vitamins; aloes; sun screens; tanning, depigmenting and shampooing agents; antiyeasts; antifungal, antibacterial and antiviral agents; topical bronchial dilators and topical cardiovascular agents; hormonal agents; vasodilators; retinoids and other dermatological agents. The hydroxycarboxylic acids and related compounds include organic alpha and beta hydroxycarboxylic acids, alpha and beta ketocarboxylic acids and salts thereof. Topical application of the cosmetic or therapeutic composition has been found to achieve a substantial increase in cosmetic or therapeutic effect of the active ingredient in humans and domesticated animals.

69 Claims, No Drawings

ADDITIVES ENHANCING THE EFFECT OF THERAPEUTIC AGENTS

This application is a continuation of application Ser. No. 08/926,030, filed Sep. 9, 1997, now U.S. Pat. No. 5,962,526.

This invention relates generally to method and composition containing hydroxyacid or related compound for enhancing therapeutic effects of cosmetic or pharmaceutical agent. As will be subsequently described in detail, we initially discovered that alpha hydroxy or keto acids and their derivatives were effective in the topical treatment of disease conditions such as dry skin, ichthyosis, eczema, palmar and plantar hyperkeratoses, dandruff, acne and warts.

We have now discovered that hydroxyacids or related compounds wherein incorporated into a therapeutic composition can substantially enhance topical effects of cosmetic and pharmaceutical agents.

In our prior U.S. Pat. No. 3,879,537 entitled "Treatment of Ichthyosiform Dermatoes" we described and claimed the use of certain alpha hydroxy acids, alpha keto acids and related compounds for topical treatment of fish-scale like ichthyotic conditions in humans. In our U.S. Pat. No. 3,920,835 entitled "Treatment of Disturbed Keratinization" we described and claimed the use of these certain alpha hydroxy acids, alpha keto acids and their derivatives for topical treatment of dandruff, acne, and palmar and plantar hyperkeratosis.

In our prior U.S. Pat. No. 4,105,783 entitled "Treatment of Dry Skin: we described and claimed the use of alpha hydroxy acids, alpha keto acids and their derivatives for topical treatment of dry skin. In our recent U.S. Pat. No. 4,246,261 entitled "Additives Enhancing Topical Corticosteroid Action" we described and claimed that alpha hydroxy acids, alpha keto acids and their derivatives, in small amounts could greatly enhance the therapeutic efficacy of corticosteroids in topical treatment of psoriasis, eczema, seborrheic dermatitis and other inflammatory skin conditions.

In our more recent U.S. Pat. No. 4,363,815 entitled "Alpha Hydroxy acids, Alpha Keto acids and Their Use in Treating Skin Conditions: we described and claimed that alpha hydroxy acids and alpha keto acids related to or originating from amino acids, whether or not found in proteins, were effective in topical treatment of skin disorders associated with disturbed keratinization or inflammation. These skin disorders include dry skin, ichthyosis, palmar and plantar hyperkeratosis, dandruff, Darier's disease, lichen simplex chronicus, keratoses, acne, psoriasis, eczema, pruritus and possibly warts and herpes.

In our most recent U.S. Pat. No. 4,518,789 entitled "Phenyl Alpha-Acyloxyacetamide Derivatives-and Their Therapeutic Use" we described and claimed that phenyl alpha acyloxyacetamide derivatives in topical or systemic administration were useful and effective for pruritus, atopic dermatitis, eczema, psoriasis, acne, dry skin, dandruff, malodors of integumental areas, various aches, pains and discomforts of skin, joints and other body parts in humans and domestic animals.

The intact skin of humans is a very effective barrier to many natural and synthetic substances. Cosmetic and pharmaceutical agents may be pharmacologically effective by systemic administration, but many of them are much less or totally ineffective on topical application to the skin. Topical effectiveness of a pharmaceutical agent depends on two major factors a) Percutaneous absorption and penetration b) Bioavailability of the penetrated pharmaceutical agent to the target site in the skin. To be therapeutically effective as a topical agent a pharmaceutical drug must penetrate the stratum corneum into the epidermal layers, distributed and bioavailable to the target sites for pharmacologic action. Many pharmacologic agents can readily penetrate the skin but they are not bioavailable to the target sites in the skin, therefore therapeutic effect is minimal and ineffective.

It has now been discovered that hydroxyacids and related compounds including those described or not described in our previous patents and additional compounds can substantially enhance the therapeutic efficacy of cosmetic and pharmaceutical agents in topical treatment of cosmetic conditions, dermatologic disorders or other afflictions. Cosmetic and pharmaceutical agents may include any chemical substances natural or synthetic, intended for topical application to the skin or its appendages in human and animals. Some examples of cosmetic and pharmaceutical agents include age spots and keratoses removing agents, analgesics, anesthetics, antiacne agents, antibacterials, antiyeast agents, antifungal agents, antiviral agents, antiburn agents, antidandruff agents, antidermatitis agents, antipruritic agents, antiperspirants, antiinflammatory agents, antihyperkeratolytic agents, antidryskin agents, antipsoriatic agents, antiseborrheic agents, astringents, softeners, emollient agents, coal tar, bath oils, sulfur, rinse conditioners, foot care agents, fungicides, hair growth promoters, hair removers, keratolytic agents, moisturizer agents, powder, shampoos, skin bleaches, skin protectants, soaps, cleansers, antiaging agents, sunscreen agents, wart removers, wet dressings, vitamins, tanning agents, topical antihistamin agents, hormones, vasodilators, retinoids, bronchial dilators, topical cardiovascular agents and other dermatologicals.

The enhancing compounds of the instant invention are hydroxycarboxylic acids and related compounds. There are three groups of such hydroxyacids. The first is hydroxymonocarboxylic acids having the following chemical structure:

$$R_1(CR_2OH)_m(C_2)_n COOH$$

wherein
$R_1$, $R_2$=H, alkyl, aralkyl or aryl group of saturated or unsaturated, straight or branched chain or cyclic form, having 1 to 25 carbon atoms.

m=1, 2, 3, 4, 5, 6, 7, 8 or 9 n=0 or a numerical number up to 23

When n=0 and m=1 or more, the hydroxymonocarboxylic acid is also called aldonic acid. The name comes from a carbohydrate, aldose, which may be oxidized to aldonic acid by the oxidation of the aldehyde group in aldose to the carboyxlic group.

The hydroxymonocarboxylic acid may be present as a free acid, lactone, or salt form. The lactone form could be either inter or intramolecular lactone, however, most common ones are intramolecular lactones with a ring structure formed by elimination of one or more water molecules between a hydroxy group and the carboxylic group. Since the hydroxymonocarboxylic acids are organic in nature, they may form a salt or a complex with an inorganic or organic base such as ammonium hydroxide, sodium or potassium hydroxide, or triethanolamine.

The hydroxymonocarboxylic acid and its related compounds may also exist as stereoisomers such as D, L, and DL forms.

The typical alkyl, aralkyl and aryl groups for $R_1$ and $R_2$ include methyl, ethyl, propyl, isopropyl, benzyl and phenyl. The hydrogen atoms of the $R_1$ and $R_2$ and $(CH_2)_n$ may be substituted by a nonfunctional element such as F, Cl, Br, I, S or a radical such as a lower alkyl or alkoxy, saturated or unsaturated, having 1 to 9 carbon atoms. Representative hydroxymonocarboxylic acids are listed below:

1. 2-Hydroxyacetic acid (Glycolic acid)
   $R_1=H$, $R_2=H$, $m=1$, $n=0$
2. 2-Hydroxypropanoic acid (Lactic acid)
   $R_1=CH_3$, $R_2=H$, $m=1$, $n=0$
3. 2-Methyl 2-hydroxypropanoic acid (Methyllactic acid)
   $R_1=CH_3$, $R_2=CH_3$, $m=1$, $n=0$
4. 2-Hydroxybutanoic acid
   $R_1=C_2H_5$, $R_2=H$, $m=1$, $n=0$
5. Phenyl 2-hydroxyacetic acid (Mandelic acid)
   $R_1=C_6H_5$, $R_2=H$, $m=1$, $n=0$
6. Phenyl 2-methyl 2-hydroxyacetic acid (Atrolactic acid)
   $R_1=C_6H_5$, $R_2=CH_3$, $m=1$, $n=0$
7. 3-Phenyl 2-hydroxypropanoic acid (Phenyllactic acid)
   $R_1=C_6H_5$, $R_2=H$, $m=1$, $n=1$
8. 2,3-Dihydroxypropanoic acid (Glyceric acid)
   $R_1=H$, $R_2=H$, $m=2$, $n=0$
9. 2, 3, 4-Trihydroxybutanoic acid
   $R_1=H$, $R_2=H$, $m=3$, $n=0$
10. 2, 3, 4, 5-Tetrahydroxypentanoic acid
    $R_1=H$, $R_2=H$, $m=4$, $n=0$
11. 2, 3, 4, 5, 6-Pentahydroxyhenxanoic acid
    $R_1=H$, $R_2=H$, $m=5$, $n=0$
12. 2-Hydroxydodecanoic acid (alpha hydroxylauric acid)
    $R_1=C_{10}H_{21}$, $R_2=H$, $m=1$, $n=0$
13. 2, 3, 4, 5, 6, 7-Hexahydroxyheptanoic acid
    $R_1=H$, $R_2=H$, $m=6$, $n=0$
14. Diphenyl 2-hydroxyacetic acid (benzilic acid)
    $R_1=C_6H_5$, $R_2=C_6H_5$, $m=1$, $n=0$
15. 4-Hydroxymandelic acid
    $R_1=C_6H_4(OH)$, $R_2=H$, $m=1$, $n=0$
16. 4-Chloromandelic acid
    $R_1=C_6H_4(Cl)$, $R_2=H$, $m=1$, $n=0$
17. 3-Hydroxybutanoic acid
    $R_1=CH_3$, $R_2=H$, $m=1$, $n=1$
18. 4-Hydroxybutanoic acid
    $R_1=H$, $R_2=H$, $m=a$, $n=2$
19. 2-Hydroxyhexanoic acid
    $R_1=C_4H_9$, $R_2=H$, $m=1$, $n=0$
20. 5-Hydroxydodecanoic acid
    $R_1=C_7H_{15}$, $R_2=H$, $m=1$, $n=3$
21. 12-Hydroxydodecanoic acid
    $R_1=H$, $R_2=H$, $m=1$, $n=10$
22. 10-Hydroxydecanoic acid
    $R_1=H$, $R_2=H$, $m=1$, $n=8$
23. 16-Hydroxyhexadecanoic acid
    $R_1=H$, $R_2=H$, $m=1$, $n=14$
24. 2-Hydroxy-3-methylbutanoic acid
    $R_1=C_3H_7$, $R_2=H$, $m=1$, $n=0$
25. 2-Hydroxy-4-methylpentanoic acid
    $R_1=C_4H_9$, $R_2=H$, $m=1$, $n=0$
26. 3-Hydroxy-4-methoxymandelic acid
    $R_1=C_6H_3(OH)(OCH_3)$, $R_2=H$, $m=1$, $n=0$
27. 4-Hydroxy-3-methoxymandelic acid
    $R_1=C_6H_3(OH)(OCH_3)$, $R_2=H$, $m=1$, $n=0$
28. 2-Hydroxy-2-methylbutanoic acid
    $R_1=C_2H_5$, $R_2=CH_3$, $m=1$, $n=0$
29. 3-(2-Hydroxyphenyl) lactic acid
    $R_1=C_6H_4(OH) CH_2$, $R_2=H$, $m=1$, $n=0$
30. 3-(4-Hydroxyphenyl) lactic acid
    $R_1=C_6H_4(OH) CH_2$, $R_2=H$, $m=1$, $n=0$
31. Hexahydromandelic acid
    $R_1=C_6H_{11}$, $R_2=H$, $m=1$, $n=0$
32. 3-Hydroxy-3-methylpentanoic acid
    $R_1=C_2H_5$, $R_2$—$CH_3$, $m=1$, $n=1$
33. 4-Hydroxydecanoic acid
    $R_1=C_6H_{13}$, $R_2=H$, $m=1$, $n=2$
34. 5-Hydroxydecanoic acid
    $R_1=C_5H_{11}$, $R_2=H$, $m=1$, $n=3$
35. Aleuritic acid
    $R_1=C_6H_{12}(OH)$, $R_2=H$, $m=2$, $n=7$ The linear lactic acid polymer is an intermolecular lactone formed by elimination of one water molecule between the hydroxy group of one molecule of lactic acid and the carboxylic group of a second molecule of lactic acid. The common linear lactic acid polymer may contain 3 lactic acid units.

Ribonic acid is one of the stereoisomers of 2, 3, 4, 5-tetrahydroxypentanoic acid, and the corresponding lactone is ribonolactone. Gluconic acid, galactonic acid, gulonic acid and mannonic acid are typical 2, 3, 4, 5, 6-pentahydroxyhexanoic acids and their corresponding lactones are gluconolactone, galactonolactone, gulonolactone and mannonolactone respectively. The related compounds of hydroxymonocarboxylic acids are ketomonocarboxylic acids which are formed from the former by a oxidation reaction or in vivo by a dehydrogenase enzyme. For example, 2-ketopropanoic acid (pyruvic acid) and 2-hydroxypropanoic acid (lactic acid) are converted to each other in vivo by the enzyme, lactate dehydrogenase. Although pure pyruvic acid (liquid form) can be kept in a refrigerator for an extended period of time a composition containing pyruvic acid for topical use is not very stable at an elevated temperature. Therefore, for practical purposes pyruvic-acid esters are used instead.

The representative esters are methyl pyruvate, ethyl pyruvate, propyl pyruvate and isopropyl pyruvate. Other representative ketomonocarboxylic acids and their esters are phenyl pyruvic acid and its esters such as methyl phenyl pyruvate, ethyl phenyl pyruvate and propyl phenyl pyruvate; formyl formic acid (2-ketoacetic acid) and its esters such as methyl, ethyl and propyl formyl formate; benzoyl formic acid and its esters such as methyl, ethyl and propyl benzoyl formate; 4-hydroxybenzoylformic acid and its esters; 4-hydroxyphenylpyruvic acid and its esters; 2-hydroxyphenylpyruvic acid and its esters.

Many hydroxy or ketomonocarboxylic acids are structurally related to amino acids either naturally occurring in proteins or not. For example alanine and pyruvic acid are interconverted to each other in vivo by an enzyme alanine dehydrogenase or alanine ketoglutarate transaminase. As mentioned earlier pyruvic acid and lactic acid are interconverted to each other in vivo by the enzyme lactate dehydrogenase. Therefore, alanine, pyruvic acid and lactic acid are chemically related in that the amino group of alanine may be converted to the keto group of pyruvic acid or the hydroxy group of lactic acid. The same relationships may apply to formyl formic acid and glycolic acid to glycine; hydroxpyruvic acid and glyceric acid to serine; phenyl pyruvic acid and phenyl lactic acid to phenylalanine; 2-keto- and 2-hydroxy-4 (methylthio) butanoic acids to methionine.

The second kind of hydroxyacid is hydroxydicarboxylic acid having the following chemical structure:

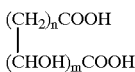

wherein m=1, 2, 3, 4, 5, 6, 7, 8 or 9 n=0 or a numerical number up to 23

The hydroxydicarboxylic acid may also be present as a free acid, lactone or salt form. The lactone form could be either inter or intramolecular lactone. However, the common lactone is an intramolecular lactone with a ring structure formed by elimination of one or more water molecule between a hydroxy group and one of the carboxylic groups. Since the hydroxydicarboxylic acid is organic in nature, it may form a salt or a complex with an inorganic or organic base such as ammonium hydroxide, sodium or potassium hydroxide, or triethanolamine.

The hydroxydicarboxylic acid and its related compounds may also exist as stereoisomers such as D, L, DL and meso forms.

The hydrogen atom attached to the carbon atom may be substituted by a nonfunctional element such as F, Cl, Br, I, S or a radical such as a lower alkyl or alkoxy of saturated or unsaturated, having 1 to 9 carbon atoms.

When n=0 and m=1 or more, the hydroxydicarboxylic acid is also called aldaric acid. The name comes from the carbohydrate, and the common ones are saccharic acid and galactaric acid. Representative hydroxydicarboxylic acids are listed below:

1. 2-Hydroxypropanedioic acid (Tartronic acid)
   m=1, n=0
2. 2-Hydroxybutanedioic acid (Malic acid)
   m=1, n=1
3. Erythraric acid and Threaric acid (Tartaric acid)
   m=2, n=0
4. Arabiraric acid, Ribaric acid, Xylaric acid and Lyxaric acid
   m=3, n=0
5. Glucaric acid (saccharic acid), Galactaric acid (Mucic acid), Mannaric acid, Gularic acid, Allaric acid, Altraric acid, Idaric acid and Talaric acid
   m=4, n=0

Commercially available saccharolactone (D-saccharic acid 1, 4-lactone) is an intramolecular lactone formed by elimination of one water molecule between the hydroxy group at position 4 and the carboxylic group at position 1.

The third type of hydroxyacid is a miscellaneous group of compounds which is not readily represented by the above generic structure of either the first type or the second type. Included in the third type of hydroxyacids are the following:

Hydroxycarboxylic acid of

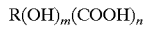

Wherein m,n=1,2,3,4,5,6,7,8,or 9

R=H, alkyl, aralkyl or aryl group of saturated or unsaturated, straight or branched chain or cyclic form, having 1 to 25 carbon atoms.

Citric acid, isocitric acid, citramalic acid, agaricic acid (n-hexadecylcitric acid), quinic acid, uronic acids including glucuronic acid, glucuronolactone, galacturonic-acid, galacturonolactone, hydroxypyruvic acid, hydroxypyruvic acid phosphate, ascorbic acid, dihydroascorbic acid, dihydroxytartaric acid, 2-hydroxy-2-methylbutanoic acid, 1-hydroxy-1-cyclopropane carboxylic acid, 2-hydroxyhexanedial, 5-hydroxylysine, 3-hydroxy-2-aminopentanoic acid, tropic acid, 4-hydroxy-2, 2-diphenylbutanoic acid, 3-hydroxy-3-methylglutaric acid, and 4-hydroxy-3-pentenoic acid.

The third type of hydroxyacid may also be present as a free acid, lactone or salt form. The lactone form could be either an inter or intramolecular lactone, however, most common are intramolecular lactones with a ring structure. Commonly known glucuronolactone is a r-lactone i.e. 1,4-lactone of intramolecular type.

The hydroxyacid of the third type may also exist as stereoisomers such as D, L, DL and meso forms. The hydrogen atom attached to the carbon atom may be substituted by a nonfunctional element such as F, Cl, Br, I, S or a radical such as a lower alkyl or alkoxy of saturated or unsaturated, having 1 to 9 carbon atoms.

Any hydroxyacid and related compound of the above three kinds may be used as an additive in a combination composition to enhance the percutaneous penetration or the therapeutic efficacy of cosmetic and pharmaceutical agents. The cosmetic and pharmaceutical agents may include but not limited to: age spots and keratoses removing agents, vitamins, aloes, retinoids, sun screens; tanning, depigmenting and shampooing agents; antiperspirants, antiyeasts, antifungal, antibacterial and antiviral agents; topical bronchial dilators; topical cardiovascular agents; keratoses, age spots and wrinkles removal agents, hair growth promoting agents and other dermatological agents.

Hydroxyacids and related compounds may also be used alone in the prophylactic and therapeutic treatment of cosmetic conditions or dermatologic disorders characterized by disturbed keratinization, aging, lipid metabolism or inflammation. The representative hydroxyacids are listed below:

Citramalic acid, tropic acid, benzilic acid, ribonic acid and ribonolactone, gulonic acid and gulonolactone, 2,3,4-trihydroxybutanoic acid, 2,3,4,5-tetrahydroxypentanoic acid, 2,3,4,5,6-pentahydroxyhexanoic acid, 2-hydroxylauric acid, 2,3,4,5,6,7-hexahydroxyheptanoic acid, aleuritic acid, 4-hydroxymandelic acid, 4-chloromandelic acid, 2-hydroxy-3-methylbutanoic acid, 2-hydroxy-4-methylpentanoic acid, 3-hydroxy-3-methylbutanoic acid, 2-hydroxy-4-methylpentanoic acid, 3-hydroxy-4-methoxymandelic acid, 4-hydroxy-3-methoxymandelic acid, 3-(2-hydroxyphenyl) lactic acid, 3-(4-hydroxyphenyl) lactic acid, hexahydromandelic acid, 3-hydroxy-3-methylpentanoic acid, 1-hydroxy-1-cyclopropane carboxylic acid, 4-hydroxybutanoic acid, 2-hydroxyhexanoic acid, 5-hydroxylauric acid, 12-hydroxylauric acid, 10-hydroxydecanoic acid, 16-hydroxyhexadecanoic acid, 4-hydroxydecanoic acid, 5-hydroxydecanoic acid, and 4-hydroxy-2, 2-diphenylbutanoic acid.

Preparation of the Therapeutic Compositions

To prepare a therapeutic composition in solution form at least one of the aforementioned enhancing compounds of hydroxyacids and a cosmetic or pharmaceutical agent are dissolved in a solution which may consist of ethanol, water, propylene glycol, acetone or other pharmaceutically acceptable vehicles. The concentration of hydroxyacids may range from 0.01 to 99 percent by weight of the total composition. The concentration of the cosmetic or pharmaceutical agent ranges from 0.01 to 40 percent by weight of the total composition.

In the preparation of a therapeutic composition in cream or ointment form at least one of hydroxyacids and one of cosmetic or pharmaceutic agents are initially dissolved in a solvent such as water, ethanol, acetone, propylene glycol or polysorbate 80. the solution thus prepared is then mixed in a conventional manner with commonly available cream or ointment base such as hydrophilic ointment or petrolatum. The concentrations of hydroxyacids, cosmetic and pharmaceutical agents may range from 0.01 to 99 percent by weight of the total composition.

Therapeutic compositions of the instant invention may also be formulated in gel, lotion, shampoo, spray, stick or powder. A typical gel composition of the instant invention utilizes at least one of hydroxyacids and one of cosmetic or pharmaceutical agents dissolved in a mixture of ethanol, water and propylene glycol in a volume ratio of 40:40:20, respectively. A gelling agent such as hydroxyethylcellulose, hydroxypropylcellulose, hydroxypropylmethylcellulose or ammoniated glycyrrhizinate is then added to the mixture with agitation. The preferred concentration of the gelling agent may range from 0.1 to 4 percent by weight of the total composition.

The following are illustrative examples of formulations and compositions according to this invention. Although the examples utilize only selected compounds and formulations, it should be understood that the following examples are illustrative and not limitative. Therefore, any of the aforementioned hydroxyacids, cosmetic and pharmaceutical agents may be substituted according to the teachings of this invention in the following examples.

EXAMPLE 1

A prophylactic and therapeutic composition in solution form for age spots and for keratoses may be prepared as follows.

Malic acid 1 gram, gluconolactone 19 grams and citric acid 0.5 gram are dissolved in a mixture of ethanol 30 ml, water 42 ml and glycerin 5 ml. Sodium bisulfite 0.5 g and hydroquinone 2 grams are added with stirring until a clear solution is obtained. The hydroxyacids, malic acid, gluconolactone and citric acid have been added a) as antioxidants to help stabilize the hydroquinone in the composition b) to enhance the penetration and the efficacy of hydroquinone c) to normalize the disturbed keratinization in age spot and keratoses.

The composition thus formulated contains 2% hydroquinone, 1% malic acid, 19% gluconolactone, 0.5% citric acid, and has pH 3.3

EXAMPLE 2

A therapeutic composition in solution form for age spots and for keratoses may be formulated as follows.

Alpha hydroxyisobutyric acid (Methyllactic acid) 20 grams and citric acid 2 grams are dissolved in a mixture of ethanol 49 ml, water 20 ml and propylene glycol 7 ml. Sodium bisulfite 0.5 g and hydroquinone 2 grams are added with stirring until a clear solution is obtained. The composition thus formulated contains 2% hydroquinone, 2% citric acid, 20% methyllactic acid, and has pH 3.6.

EXAMPLE 3

A prophylactic and therapeutic composition containing minoxidil and lactic acid for hair growth and for prevention of hair loss on the scalp may be formulated as follows.

Minoxidil 2 grams and lactic acid 3 ml are dissolved in a mixture of ethanol 80 ml and propylene glycol 15 ml with stirring until a clear solution is obtained. The composition thus formulated contains 2% minoxidil, 3% lactic acid, and has pH 4.7. The lactic acid has been added to help minoxidil dissolved into solution, to enhance the penetration and the efficacy of minoxidil for hair growth.

EXAMPLE 4

A prophylactic and therapeutic composition in solution form for hair growth on the scalp may be formulated as follows.

Minoxidil 2 grams and ethyl pyruvate 2 ml are dissolved in a mixture of ethanol 80 ml and propylene glycol 16 ml. The composition thus formulated contains 2% minoxidil, 2% ethyl pyruvate, and has pH 5.0. The ketoacid ester, ethyl pyruvate has been added to enhance the penetration and the efficacy of minoxidil for hair growth on the scalp.

EXAMPLE 5

A therapeutic composition containing anthralin and hydroxyacid for psoriasis may be formulated as follows.

Anthralin powder 0.5 gram and alpha hydroxyisobutyric acid 4 grams are dissolved in a mixture of ethanol 50 ml, acetone 30 ml and diisopropyl adipate 16 ml with stirring until a clear yellowish solution is obtained. The composition thus formulated contains 0.5% anthralin, 4% alpha hydroxyisobutyric acid, and has pH 4.2. The hydroxyacid has been added to enhance the penetration and the efficacy of anthralin for psoriasis.

EXAMPLE 6

A therapeutic composition containing thionicotinamide and hydroxyacid for psoriasis, keratoses and warts may be formulated as follows.

Thionicotinamide 2 grams and lactic acid 20 ml are dissolved in a mixture of ethanol 40 ml , water 30 ml and propylene glycol 8 ml with stirring until a clear yellowish solution is obtained. The composition thus formulated contains 2% thionicotinamide, 20% lactic acid, and has pH 3.3. The lactic acid has been added to enhance the penetration and the efficacy of thionicotinamide, and also to normalize the disturbed keratinization in psoriasis, keratoses and warts

EXAMPLE 7

A therapeutic composition containing 6-aminonicotinamide and hydroxyacid for psoriasis, keratoses and warts may be formulated as follows.

6-Aminonicotinamide 1 gram and glycolic acid 19 grams are dissolved in a mixture of ethanol 40 ml, water 32 ml and propylene glycol 8 ml with stirring until a clear solution is obtained. The composition thus formulated contains 1% 6-aminonicotinamide, 19% glycolic acid, and has pH 3.0. The glycolic acid has been added to enhance the penetration and the efficacy of 6-Aminonicotinamide, and also to normalize the disturbed keratinization in psoriasis, keratoses and warts.

EXAMPLE 8

A therapeutic composition containing clotrimazole and hydroxyacid for fungal infection may be formulated as follows.

Clotrimazole 1 gram and lactic acid 4 ml are dissolved in 4 ml of ethanol, and the solution thus obtained is mixed with 91 grams of hydrophilic ointment USP. The mixing is continued until a uniform consistency is obtained. The composition thus formulated contains 1% clotrimazole, 4% lactic acid, and has pH 3.2. The lactic acid has been added to enhance the penetration and the efficacy of clotrimazole for athlete's foot, and also to speed up healing and normalize the disturbed keratinization.

EXAMPLE 9

A prophylactic and therapeutic composition containing chlorhexidine and hydroxyacid as general antiseptics on skin, and for prophylactic and therapeutic treatment of acne may be formulated as follows. Chlorhexidine diacetate 1 gram and benzilic acid 5 grams are dissolved in a mixture of ethanol 70 ml, water 10 ml and propylene glycol 14 ml with stirring until a clear solution is obtained. The composition thus formulated contains 1% chlorhexidine, 5% benzilic acid, and has pH 4.4. Benzilic acid has been added to enhance the antibacterial effect of chlorhexidine, to eliminate the oiliness of the skin, and to improve the acne lesions.

EXAMPLE 10

A prophylactic and therapeutic composition containing benzilic acid as the only active ingredient for oily skin, acne, skin cleansing and skin malodor may be formulated as follows.

Benzilic acid 7 grams is dissolved in a mixture of ethanol 60 ml, water 20 ml and propylene glycol 13 ml with stirring until a clear solution is obtained. The composition thus prepared contains 7% benzilic acid, and has pH 3.0.

EXAMPLE 11

A therapeutic composition containing tropic acid as the only active ingredient for severe dry skin may be formulated as follows.

Tropic acid 10 grams is dissolved in 20 ml of ethanol, and the solution thus obtained is mixed with 70 grams of hydrophilic ointment USP. The mixing is continued until a uniform consistency is obtained. The composition thus formulated contains 10% tropic acid as an active ingredient, and has pH 3.7.

EXAMPLE 12

A prophylactic and therapeutic composition containing ribonolactone as the only active ingredient for oily skin, acne and skin cleansing may be formulated as follows.

Ribonolactone 4 grams is dissolved in a mixture of ethanol 36 ml and water 60 ml with stirring until a clear solution is obtained. The composition thus prepared contains 4% ribonolactone as an active ingredient, and has pH 3.8.

EXAMPLE 13

A therapeutic composition containing hydrocortisone and tropic acid for inflammatory and/or pruritic skin disorders may be formulated as follows.

Hydrocortisone 0.5 gram and tropic acid 5 grams are dissolved in 10 ml of ethanol and 4 ml of acetone, and the solution thus obtained is mixed with 80 grams of hydrophilic ointment USP. The mixing is continued until a uniform consistency is obtained. The composition thus formulated contains 0.5% hydrocortisone and 5% tropic acid as active ingredients, and has pH 3.4. The tropic acid has been added to enhance the penetration and the efficacy of hydrocortisone and also to normalize the disturbed keratinization.

EXAMPLE 14

A therapeutic composition containing triamcinolone acetonide and benzilic acid for eczema, psoriasis and other inflammatory and pruritic skin disorders may be formulated as follows.

Triamcinolone acetonide 0.1 gram and benzilic acid 5 grams are dissolved in 10 ml of ethanol, and the solution thus obtained is mixed with 85 grams of hydrophilic ointment USP. The mixing is continued until a uniform consistency is obtained. The composition thus formulated contains 0.1% triamcinolone acetonide, 5% benzilic acid, and has pH 3.4. The benzilic acid has been added to enhance the penetration and the efficacy of triamcinolone acetonide, and also to normalize the disturbed keratinization in eczema, psoriasis and other inflammatory skin disorders.

EXAMPLE 15

A prophylactic and therapeutic composition containing dipyridamole and lactic acid for hair growth and for prevention of hair loss on the scalp may be formulated as follows.

Dipyridamole 2 grams and lactic acid 4 ml are dissolved in a mixture of ethanol 80 ml and propylene glycol 14 ml with stirring until a clear yellowish solution is obtained. The composition thus formulated contains 2% dipyridamole, 4% lactic acid, and has pH 4.4. The lactic acid has been added to help dipyridamole dissolved into solution, to enhance the penetration and the efficacy of dipyridamole for hair growth and for preventing hair loss.

EXAMPLE 16

A therapeutic composition containing clobetasol propionate and agaricic acid for eczema, psoriasis and other inflammatory and pruritic skin disorders may be formulated as follows.

Agaricic acid fine powder 2 grams and 98 grams of clobetasol propionate cream are mixed until a uniform consistency is obtained. The composition thus formulated contains approximately 0.05% clobetasol propionate, 2% agaricic acid, and has pH 4.3. The agaricic acid has been added to enhance the penetration and the efficacy of clobetasol propionate, and also to normalize the disturbed keratinization in eczema, psoriasis and other inflammatory skin disorders.

EXAMPLE 17

A therapeutic composition containing betamethasone dipropionate and benzilic acid for eczema, psoriasis, contact dermatitis and other inflammatory and pruritic skin disorders may be formulated as follows.

Benzilic acid powder 5 grams and 95 grams of betamethasone dipropionate ointment are mixed until a uniform consistency is obtained. The composition thus formulated contains approximately 0.05% betamethasone dipropionate and 5% benzilic acid. The benzilic acid has been added to enhance the penetration and the efficacy of betamethasone dipropionate, and also to normalize the disturbed keratinization in eczema, psoriasis and other inflammatory skin disorders.

EXAMPLE 18

A prophylactic and therapeutic composition containing aloe, malic acid and gluconolactone for oily skin and acne may be formulated as follows.

Aloe powder 200 fold 0.2 gram and ammoniated glycyrrhizinate 2 grams are mixed with water 61 ml and propylene glycol 2 ml. The mixture is heated to 50° C. until the aloe powder and the ammoniated glycyrrhizinate are completely dissolved. Ethanol 10 ml is added to the solution followed by the addition of partially neutralized malic acid stock solution 3 ml and gluconolactone stock solution 22 ml with stirring. The warm solution is poured into container jars before cooling. The gel composition thus formulated contains 40% aloe, 1% malic acid, 9% gluconolactone, and has pH 4.0. Malic acid and gluconolactone have been added to enhance the skin softness and smoothness by aloe, and also to normalize any disturbed keratinization of the skin.

EXAMPLE 19

A sun screen composition containing Octyl dimethyl PABA, dioxybenzone and lactic acid may be formulated as follows. Octyl dimethyl PABA 5 grams, dioxybenzone 3 grams and lactic acid 2 ml are dissolved in a mixture of ethanol 65 ml, water 10 ml and propylene glycol 15 ml with stirring until a clear solution is obtained. The composition thus formulated contains 5% octyl dimethyl PABA, 3% dioxybenzone, 2% lactic acid, and has pH 3.6. The lactic acid has been added to substantiate the absorption of sun-screen agents, octyl dimethyl PABA and dioxybenzone, and to enhance the sun screen effect.

EXAMPLE 20

A prophylactic and therapeutic composition containing tetracycline and glycolic acid for oily skin and-acne may be formulated as follows.

Tetracycline 3 grams and glycolic acid 5 grams are dissolved in a mixture of ethanol 40 ml, water 40 ml and propylene glycol 12 ml with stirring until the tetracycline and glycolic acid are completely dissolved. The composition thus formulated contains 3% tetracycline, 5% glycolic acid, and has pH 3.4. The glycolic acid has been added to help tetracycline dissolved into the solution, to enhance the penetration and the efficacy of tetracycline, and to normalize the disturbed keratinization in acne.

EXAMPLE 21

A therapeutic composition containing griseofulvin and methyl pyruvate for fungal infection of nails may be formulated at follows.

Griseofulvin 1 gram and methyl pyruvate 2 ml are dissolved in a mixture of 2-pyrrolidone 20 ml. PEG-400 47 ml and ethanol 30 ml with stirring until the griseofulvin is completely dissolved. The composition thus formulated contains 1% griseofulvin, 2% methyl pyruvate, and has pH 4.4. The methyl pyruvate has been added to help griseofulvin dissolve into the solution, to enhance the penetration and the efficacy of griseofulvin, and to normalize the disturbed keratinization in nails.

EXAMPLE 22

A therapeutic composition containing lidocaine and atrolactic acid for pruritic skin may be formulated as follows.

Lidocaine 2 grams and atrolactic acid hemihydrate 3 grams are dissolved in a mixture of ethanol 40 ml, water 40 ml and propylene glycol 15 ml with stirring until the lidocaine and atrolactic acid are completely dissolved. The composition thus formulated contains 2% lidocaine, 3% atrolactic acid, and has pH 4.6. The atrolactic acid has been added-to help lidocaine dissolved and stabilized in the solution and to enhance the efficacy of lidocaine for pruritic skin.

EXAMPLE 23

A prophylactic and therapeutic composition containing retinoic acid and ethyl pyruvate for oily skin and acne may be formulated as follows.

Retinoic acid, all-trans 0.1 gram and ethyl pyruvate 2 ml are dissolved in a mixture of ethanol 80 ml, water 10 ml and propylene glycol 8 ml with stirring until a yellowish solution is obtained. The composition thus formulated contains 0.1% vitamin A acid, 2% ethyl pyruvate, and has pH 3.6. The ethyl pyruvate has been added to enhance the penetration and the efficacy of retinoic acid, and to normalize the disturbed keratinization in acne.

EXAMPLE 24

A prophylactic and therapeutic composition containing erythromycin and aleuritic acid for oily skin and acne may be formulated as follows.

Erythromycin 2 grams and aleuritic acid 2 grams are dissolved in a mixture of ethanol 50 ml, water 40 ml and propylene glycol 6 ml with stirring until a clear solution is obtained. The composition thus formulated contains 2% erythromycin, 2% aleuritic acid, and has pH 5.7. The aleuritic acid has been added to help erythromycin dissolve into the solution, to enhance the penetration and the efficacy of erythromycin, and to normalize the disturbed keratinization in acne.

EXAMPLE 25

A therapeutic composition containing P-hydroxymandelic acid for dry skin may be formulated as follows.

P-Hydroxymandelic acid 10 grams is dissolved in 20 ml of ethanol, and the pinkish solution thus obtained is mixed with 70 grams of hydrophilic ointment USP with stirring until a uniform consistency is obtained. The composition thus formulated contains 10% P-hydroxymandelic acid as an active ingredient, and has pH 3.2. P-Hydroxymandelic acid has been incorporated into the composition to alleviate any scaly or flaky skin, and to change the dry skin into normal smooth and soft skin.

EXAMPLE 26

A therapeutic composition containing hydroquinone and lactic acid in solution form for age spots, keratoses, melasmas, lentigines and other pigmented skin spots may be formulated as follows.

Lactic acid 10 ml, hydroquinone 4 grams and sodium metabisulfite 0.6 gram are dissolved in a mixture of ethanol 70 ml, water 10 ml and propylene glycol 6 ml with stirring until a clear solution is obtained. The composition thus formulated contains 4% hydroquinone, 10% lactic acid, and has pH 4.0. The lactic acid has been added to help stabilize and enhance the penetration and the efficacy of hydroquinone, and also to normalize the disturbed keratinization in the skin lesions. The composition thus formulated is packaged in felt pens for controlled delivery to skin lesions.

EXAMPLE 27

A therapeutic composition containing hydroquinone and glycolic acid in solution form for age spots, keratoses, melasmas, lentigines and other pigmented skin spots may be formulated as follows.

Glycolic acid 8 grams, hydroquinone 5 grams and sodium metabisulfite 0.5 gram are dissolved in a mixture of ethanol 70 ml, water 10 ml and propylene glycol 7 ml with stirring until a clear solution is obtained. The composition thus formulated contains 5% hydroquinone, 8% glycolic acid, and has pH 3.9. The glycolic acid has been added to help stabilize and enhance the penetration and the efficacy of hydroquinone, and also to normalize the disturbed keratinization in the skin lesions. The composition thus prepared is packaged in felt pens for controlled delivery to skin lesions.

EXAMPLE 28

A therapeutic composition containing hydroquinone and 2-methyl 2-hydroxypropanoic acid in solution form for age spots, keratoses, melasmas, lentigines and other pigmented skin spots may be formulated as follows.

2-Methyl 2-hydroxypropanoic acid 12 grams, hydroquinone 4 grams and sodium bisulfite 0.3 gram are dissolved in a mixture of ethanol 60 ml, water 20 ml and propylene glycol 4 ml with stirring until a clear solution is obtained. The composition thus formulated contains 4% hydroquinone, 12% 2-methyl 2-hydroxypropanoic acid, and has pH 4.0. The composition solution is packaged in felt pens for controlled delivery to skin lesions. The 2-methyl 2-hydroxypropanoic acid has been added to help stabilize and enhance the penetration and the efficacy of hydroquinone, and also to normalize the disturbed keratinization in the skin lesions.

EXAMPLE 29

A composition containing hydroquinone alone in solution form for age spots and keratoses studies may be formulated as follows.

Hydroquinone 5 grams and sodium metal bisulfite 0.5 gram are dissolved in a mixture of ethanol 70 ml, water 15 ml and propylene glycol 10 ml with stirring until a clear solution is obtained. The composition thus prepared contains 5% hydroquinone and has pH 6.0. The composition solution is packaged in felt pens for comparative studies; with or without hydroxyacids on age spots and keratoses.

Test Results

In order to determine whether addition of a hydroxyacid in the composition could enhance the therapeutic action of a cosmetic or pharmaceutical agent a total of more than 55 volunteers and patients having different skin disorders participated in these studies. Each participating subject was given two preparations; i.e. with or without the addition of a hydroxyacid in the therapeutic composition.

Topical applications were carried out either by bilateral or sequential comparison, In bilateral comparison the subject was instructed to apply one preparation on one side of the body and the other one on the other side of the body. For psoriasis, eczema, severe dry skin, athlete's foot, etc., where both sides were involved, the subject was instructed to apply two to three times daily one medication on one side of the body for a period of up to several months of time. In the pulse treatment for psoriasis or other inflammatory diseases the medication was applied only once every three days or twice a week. The medication was discontinued whenever a total remission of the lesions occurred prior to the test period of up to several months.

For the scalp or face involvement such as in dandruff, oily skin, acne and seborrheic dermatitis the subject was instructed to apply two to three time daily one medication on one side of the scalp or the face and the other medication on the other side of the scalp or the face for a period of up to 12 weeks of time. For age spots, keratoses or warts the medication was continued for up to 4 months of time.

Sequential administrations of medications were carried out whenever the bilateral comparison was difficult, for example in pruritic conditions the subject was instructed to apply four time daily or as often as necessary one medication on the pruritic lesions for two days, then switched to the other medication on the same lesions for another two days, thus to compare which medication was more effective in relieving the itching.

1. Dry skin

Human subjects having ordinary dry skin or with moderate degrees of dry skin as evidenced by dry, flaking and cracking of the skin were instructed to apply topically the lotion, cream or ointment containing 3 to 7 percent of hydroxyacids of the instant invention on the affected skin areas. Topical application, two to three times daily, was continued for two to three weeks. In all the nine subjects tested, the feeling of the skin dryness disappeared within a week of topical application. The rough and cracked skin became less pronounced and the skin appeared normal and felt smooth after 10 days of topical treatment.

The ordinary dry skin conditions once restored to normal appearing skin remained improved for some time until causes of dry skin, such as low humidity, cold weather, excessive contact pressure, detergents, soaps, solvents, chemicals, etc., again caused recurrence of the dry skin condition. On continued use it was also found that twice daily topical application of a composition containing one or more hydroxyacids of instant invention prevented the development of new dry skin lesions.

In severe dry skin the skin lesions are different from the above. The involved skin is hyperplastic, fissured and has thick adherent scales. The degree of thickening is such that lesions are palpably and visually elevated. The thickened adherent scales cause the surface of involved skin to be markedly rough and uneven. The two attributes of thickness and texture can be quantified to allow objective measurement of degree of improvement from topically applied therapeutic test materials as follows:

|  | DEGREE OF IMPROVEMENT | | | | |
| --- | --- | --- | --- | --- | --- |
|  | None (0) | Mild (1+) | Moderate (2+) | Substantial (3+) | Complete (4+) |
| THICKNESS | Highly elevated | Detectable reduction | Readily apparent reduction | Barely elevated | Normal thickness |

| | DEGREE OF IMPROVEMENT | | | | |
|---|---|---|---|---|---|
| | None (0) | Mild (1+) | Moderate (2+) | Substantial (3+) | Complete (4+) |
| TEXTURE | Visibly rough | Palpably rough | Uneven but not rough | Slightly uneven | Visibly and palpably smooth |

By means of such parameters degrees of change in lesions can be numerically noted and comparisons made of one treated site to another.

In order to evaluate the hydroxyacids and their related compounds of the instant invention a total of six patients with severe dry skin conditions or ichthyosis were treated with the compositions containing 7 to 15% of hydroxyacids as described in the Examples.

Treated areas were of a size convenient for topical applications, i.e., circles 5 cm in diameter demarcated with a plastic ring of that size inked on a stamp pad. The medicinal creams or ointments were topically applied by the patient in an amount sufficient to cover the treatment sites. Applications were made three time daily and without occlusive dressings. Applications were discontinued at any time when resolution of the lesion on the treatment area was clinically judged to be complete.

The test results on patients with severe dry skin are summarized on the following table.

| Topical Effectiveness of Hydroxyacids on Severe Dry Skin | | |
|---|---|---|
| Compounds | Number of Patients | Therapeutic Effectiveness |
| 1. Tropic acid | 4 | 4+ |
| 2. Benzilic acid | 5 | 4+ |
| 3. Ribonolactone | 3 | 3+ |
| 4. 4-Hydroxymandelic acid | 2 | 3+ |
| 5. 3-Chloro 4-hydroxymandelic acid | 2 | 3+ |
| 6. 3,4-Dihydroxymandelic acid | 2 | 3+ |

2. Psoriasis

The involved skin in psoriasis is hyperplastic (thickened), erythematous (red or inflamed), and has thick adherent scales. The degree of thickening is such that lesions are elevated up to 1 mm above the surface of adjacent normal skin; erythema is usually an intense red; the thickened adherent scales cause the surface of involved skin to be markedly rough and uneven. These three attributes of thickness, color and texture can be quantified to allow objective measurement of degree of improvement from topically applied therapeutic test materials as follows.

| | DEGREE OF IMPROVEMENT | | | | |
|---|---|---|---|---|---|
| | None (0) | Mild (1+) | Moderate (2+) | Substantial (3+) | Complete (4+) |
| Thickness | Highly elevated | Detectable reduction | Readily apparent | Barely elevated | Normal thickness |
| Texture | Visibly rough | Palpably rough | Uneven but not rough | Slightly uneven | Visibly and palpably smooth |
| Color | Intense red | Red | Dark Pink | Light pink | Normal skin color |

By means of such parameters degree of improvements in psoriatic lesions can be numerically recorded and comparisons made of one treated site to another. The treatment schedule was quite different from the previously described in that the present study was employing a "Pulse Treatment." Instead of several times daily application the therapeutic composition of antipsoriatic agent with or without a hydroxyacid in solution form was topically applied to the involved skin only once in every three days or twice a week. The test results on patients having psoriasis are summarized on the following table.

| Topical Effects on Psoriasis of Antipsoriatic Agents With or without Hydroxyacids | | |
|---|---|---|
| Compositions | Number of Patients | Therapeutic Effectiveness |
| Thionicotinamide 3% alone | 6 | 2+ |
| with 10% Lactic acid | 6 | 4+ |
| with 5% Glycolic acid | 4 | 4+ |
| with 5% 2-methyl 2-hydroxypropanoic acid | 3 | 4+ |
| 6-Aminonicotinamide 1% alone | 5 | 3+ |
| with 10% Lactic acid | 5 | 4+ |
| with 10% Glycolic acid | 4 | 4+ |
| Betamethasone dipropionate 0.05% ointment alone | 5 | 3+ |
| with 5% Benzilic acid | 4 | 4+ |
| with 5% Tropic acid | 3 | 4+ |
| with 5% 2-Methyl 2-Hydroxypropanoic acid | 3 | 4+ |
| Clobetasol propionate 0.05% cream alone | 4 | 2+ |
| with 5% Benzilic acid | 3 | 3+ |
| with 5% Tropic acid | 2 | 3+ |
| with 5% 2-Methyl 2-hydroxypropanoic acid | 3 | 3+ |

In a topical treatment of eczema patients, betamethasone dipropionate or clobetasol propionate alone at 0.05% would achieve only a 3+ improvement on all the eczema patients tested. As shown by the table with the additional of 5% gluconolactone or ribonolactone betamethasone dipropionate or clobetasol propionate could attain a 4+ maximal clearing on all the eczema patients tested.

Topical Effects on Eczema of Corticosteroids
With and Without Hydroxyacid Lactone

| Composition | Number of Patients | Therapeutic Effectiveness |
| --- | --- | --- |
| Betamethasone dipropionate 0.05% alone | 3 | 3+ |
| with 5% Gluconolactone | 3 | 4+ |
| with 5% Ribonolactone | 2 | 4+ |
| Clobetasol propionate 0.05% alone | 4 | 3+ |
| with 5% Gluconolactone | 4 | 4+ |
| with 5% Ribonolactone | 3 | 4+ |

3. Age Spots, Wrinkles, Keratoses and Pigmented Skin Lesions

Therapeutic compositions packaged in felt pens as described in Examples were provided to 14 patients for treatment of age spots, wrinkles, keratoses and other pigmented skin spots. Each participating patient received two felt pens; i.e. with or without the addition of hydroxyacid to the composition containing hydroquinone. The patients were instructed to apply topically one medication on one side of the body such as on the back of the left hand and the other medication on the other side of the body such as on the back of the right hand. Specific instructions were given to the patients that the medications were applied twice daily and discretely only to the skin lesions of age spots, wrinkles, keratoses, melasmas, lentigines or other pigmented skin spots.

Within one to three weeks, improvement of age spots and keratoses was clinically discernible. After one to three months substantial eradication of age spots, wrinkles and keratoses occurred in all the patients tested. Complete eradication of age spots usually occurred within two to four months of topical administration in most cases. Therapeutic compositions containing higher concentrations of hydroxyacids (10 to 20%) and hydroquinone (3 to 5%) were judged to be more efficient in eradicating age spots, wrinkles and keratoses within shorter periods of time. Without the addition of a hydroxyacid to the composition of hydroquinone, eradication of age spots, wrinkles or keratoses did not occur within four months of time.

It was also found that while compositions containing hydroxyacids without hydroquinone were effective for eradication of keratoses and wrinkles, the compositions were not efficient in eradicating pigmented age spots, melasmas or lentigines within 4 months of time. In any case, with the addition of a hydroxyacid to the composition containing hydroquinone, pigmented age spots, melasmas, lentigines and other pigmented skin spots had been substantially eradicated.

4. Acne

Therapeutic compositions containing tetracycline, erythromycin or chlorhexidine with or without the addition of a hydroxyacid were provided to 9 patients having papulopustular or pustular lesions of acne. Each participating patient received two medications, with or without the addition of a hydroxyacid to the composition containing an antibiotic. The patients were instructed to apply topically one medication on one side of the body such as the left side forehead, face, back or chest, and the other medication on the other side of the body such as right side forehead, face, back or chest. Twice daily administration was continued for 4 to 12 weeks.

The degree and rate of improvement on acne lesions were clinically evaluated, and comparison was made between the two sides; one side with and the other side without a hydroxyacid in the compositions containing an antibiotic. It was found that the degree and rate of improvement on acne lesions were substantially better on the side treated with a combination composition containing both the hydroxyacid and the antibiotic as compared to that of the antibiotic alone. The time for complete clearing of acne lesions treated with a combination composition varied from 4 to 12 weeks of time, with an average time of 8 weeks, whereas complete clearing with that of the antibiotic alone ranged from 8 weeks to 9 months, with an average of 4 months.

5. Preventing Hair Loss And For Hair Growth

Prophylactic and therapeutic compositions containing minoxidil or dipyridamole with or without a hydroxyacid or related compound were provided to 6 human subjects having a progressive loss of hair on the scalp. Each participating subject received two medications; i.e. with or without the addition of a hydroxyacid to the composition containing minoxidil or dipyridamole. The subjects were instructed to apply topically one medication on one side of the scalp and the other medication on the other side of the scalp. Twice daily topical applications were continued for 2 to 6 months. Clinical evaluation shows that the combination compositions containing minoxidil or dipyridamole and a hydroxyacid or related compound were therapeutically more efficient in preventing the hair loss and enhancing hair growth on the scalp.

Therapeutic compositions containing clotrimazole or griseofulvin with or without the addition of a hydroxyacid were provided to 6 patients having recurrent fungal infections of the foot; i.e. athlete's foot with or without toe nail involvement. Each participating patient received two medications with or without the addition of a hydroxyacid to the composition containing clotrimazole or griseofulvin. The patients were instructed to apply topically one medication on one side of the body such as left foot, and the other medication on the other side of the body such as right foot. Three time daily applications were continued for one to two weeks. When nail infections were involved the topical application was continued for up to 4 months using the compositions containing griseofulvin with or without the addition of a hydroxyacid.

The degree and rate of improvement on skin lesions were clinically evaluated, and comparison was made one side of the body against the other. It was found that the skin lesions improved much faster with the compositions containing both the antifungal agent and the hydroxyacid. The presence of hydroxyacid appeared to enhance the efficacy of the antifungal agent, and also to eliminate the discomforts such as itching, tingling, burning and heat due to the fungal infection. Generally the infected skin healed within a week from topical application of the compositions containing an antifungal agent and a hydroxyacid. When toe nails were involved in the fungal infection the complete healing and regrowth of nails usually took several months on continued topical application of medications containing griseofulvin and a hydroxyacid.

The hydroxyacids and related compounds which may be useful as dermatologic agents for various conditions and disorders including age spots, keratoses, skin wrinkles etc. or as additives to enhance therapeutic effects of other cosmetic or pharmaceutical agents include 2-Hydroxyacetic acid; 2-hydroxypropanoic acid; 2-methyl 2-hydroxypropanoic acid; 2-hydroxybutanoic acid: phenyl 2-hydroxyacetic acid; phenyl 2-methyl 2-hydroxyacetic acid; 3-phenyl 2-hydroxyacetic acid; 2,3-dihydroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxymandelic acid; 4-hydroxy-3-methoxymandelic acid; 2-hydroxy-2-methylbutanoic acid; 3-(2-hydroxphenyl) lactic acid: 3-(4-hydroxyphenyl) lactic acid; hexahydromandelic acid; 3-hydroxy-3-methylpentanoic acid; 4-hydroxydecanoic acid; 5-hydroxydecanoic acid; aleuritic acid.

2-Hydroxypropanedioic acid; 2-hydroxybutanedioic acid; erythraric acid: threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutanedioic acid.

Citric acid, isocitric acid, agaricic acid, quinic acid, glucuronic acid, glucuronolactone, galacturonic acid, galacturonolactone, uronic acids, uronolactones, ascorbic acid, dihydroascorbic acid, dihydroxytartaric acid, tropic acid, ribonolactone, gluconolactone, galactonolactone, gulonolactone, mannonolactone, citramalic acid.

Pyruvic acid, hydroxypyruvic acid, hydroxypyruvic acid phosphate, their esters; methyl pyruvate, ethyl pyruvate, propyl pyruvate, isopropyl pyruvate; phenyl pyruvic acid, its esters; methyl phenyl pyruvate, ethyl phenyl pyruvate, propyl phenyl pyruvate; formyl formic acid; its esters; methyl formyl formate, ethyl formyl formate, propyl formyl formate; benzoyl formic acid, its esters; methyl benzoyl formate, ethyl benzoyl formate and propyl benzoyl formate; 4-hydroxybenzoyl formic acid, its esters; 4-hydroxyphenyl pyruvic acid, its esters; 2-hydroxyphenyl pyruvic acid and its esters.

The invention may be embodied in other specific forms without departing from the spirit or essential characteristics thereof. The present embodiments are therefore to be considered in all respects as illustrative and not restrictive, the scope of the invention being indicated by the appended claims and all changes which come within the meaning and equivalency of the claims are therefore intended to be embraced therein.

What is claimed is:

1. A topically effective skin treating composition prepared by:

combining, simultaneously or in any order, at least one first ingredient with at least one second ingredient;

said first ingredient selected from the group consisting of anti-psoriatic agents, anti-dermatitis agents, anti-inflammatory agents other than topical corticosteriods, antihistamines, anti-pruritic agents and local anesthetics;

said second ingredient comprising an enhancing amount of at least one member selected from the group consisting of hydroxycarboxylic acids, lactones and salts thereof and related ketocarboxylic acids, esters, and salts thereof.

2. The composition as claimed in claim 1, wherein said second ingredient is selected from the group consisting of a hydroxymonocarboxylic acid, a hydroxydicarboxylic acid or a related compound;

said hydroxymonocarboxylic acid being at least one member selected from the group having the following chemical structure:

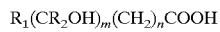

wherein $R_1$, $R_2$=H, alkyl, arakyl or aryl group of saturated or unsaturated, straight or branched chain having 1 to 25 carbon atoms, or cyclic form, m=1, 2, 3, 4, 5, 6, 7, 8 or 9 n=0 or a numerical number up to 23 present as a free acid, lactone or salt form, and as optically active or inactive isomer such as D, L, and DL forms; the hydrogen atom attached to the carbon atom may be substituted by F, Cl, Br, I, or S atom or a lower alkyl or alkoxy saturated or unsaturated radical, having 1 to 9 carbon atoms;

said hydroxydicarboxylic acid being at least one member selected from the group having the following chemical structure:

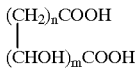

wherein m=1, 2, 3, 4, 5, 6, 7, 8, or 9 n=0 or a numerical number up to 23 present as free acid, lactone or salt form, and as optically active or inactive D, L, and meso isomer; hydrogen atom attached to the carbon atom may be substituted by F, Cl, Br, I, or S atom or a lower alkyl or alkoxy saturated or unsaturated radical, having 1 to 9 carbon atoms; and said related compound being at least one member selected from the group having the following chemical structure:

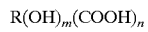

wherein

R=H, alkyl, aralkyl, or aryl group of saturated or unsaturated straight or branched chain, having 1 to 25 carbon atoms, or cyclic form, m and n=1, 2, 3, 4, 5, 6, 7, 8 or 9 present as free acid, lactone or salt form, and as optically active or inactive D, L, and meso isomer; hydrogen atom attached to the carbon atom maybe substituted by F, Cl, Br, I, or S atom or a lower alkyl or alkoxy saturated or unsaturated radical, having 1 to 9 carbon atoms.

3. The composition as claimed in claim 1, wherein said second ingredient is selected from the group consisting of 2-hydroxyacetic acid (glycolic acid), 2-hydroxypropanoic acid (lactic acid), 2-methyl 2-hydroxypropanoic acid (methyllactic acid), phenyl 2-hydroxyacetic acid (mandelic acid), diphenyl 2-hydroxyacetic acid (benzilic acid), citric acid, pyruvic acid, ethyl pyruvate, methyl pyruvate, malic acid, tartaric acid, gluconic acid, gluconolactone, ribonic acid, ribonolactone, 4-hydroxymandelic acid, quinic acid, galactonic acid, galactonolactone, gulonic acid, gulonolactone, galacturonic acid, and galacturonolaction.

4. The composition as claimed in claim 1, wherein said second ingredient is selected from the group consisting of phenyl 2-methyl 2-hydroxyacetic acid (atrolactic acid), 3-phenyl 2-hydroxypropanoic acid (phenyllactic acid), propyl pyruvate, isopropyl pyruvate, tropic acid, saccharic acid, trethocanic acid, pantoic acid, pantoyllactone, mucic acid, isocitric acid, citramalic acid, agaricic acid, aleuritic acid, erythronic acid, erythronolactone, and ascorbic acid.

5. The composition as claimed in claim 1, wherein said second ingredient is a hydroxycarboxylic acid.

6. The composition as claimed in claim 1 wherein said second ingredient is glycolic acid.

7. The composition as claimed in claim 1, wherein said second ingredient is lactic acid.

8. The composition as claimed in claim 1, wherein said second ingredient is citric acid.

9. The composition as claimed in claim 1, wherein said second ingredient is 2-methyl 2-hydroxypropanoic acid.

10. The composition as claimed in claim 1, wherein said second ingredient is gluconic acid or gluconolactone.

11. The composition as claimed in claim 1, wherein said second ingredient is ribonic acid or ribonolactone.

12. The composition as claimed in claim 1, wherein said second ingredient is mandelic acid or 4-hydroxymandelic acid.

13. The composition as claimed in claim 2 wherein said second ingredient is present as a salt with an organic base or an inorganic alkali.

14. The composition as claimed in claim 1, wherein said first ingredient is selected from the group consisting of coal tar, anthralin, lidocaine, sulfur, selenium sulfide, zinc pyrithione, crotamiton, cromolin, procaine, and retinoids.

15. The composition as claimed in claim 1, wherein said first ingredient is coal tar.

16. The composition as claimed in claim 1, wherein said first ingredient is an anti-psoriatic agent selected from the group consisting of coal tar, anthralin, retinoids, sulfur, selenium sulfide and zinc pyrithione.

17. The composition as claimed in claim 1, wherein said first ingredient is an anti-psoriatic agent selected from the group consisting of retinoic acid, 13-cis-retinoic acid, retinyl acetate, retinyl palmitate, retinol, and tazarotene.

18. The composition as claimed in claim 16, wherein said first ingredient is anthralin.

19. The composition as claimed in claim 1, wherein said first ingredient is an anti-pruritic agent selected from the group consisting of menthol, camphor, phenol, calamine, crotamiton, and doxepin.

20. The composition as claimed in claim 1, wherein said first ingredient is a local anesthetic selected from the group consisting of pramoxine, procaine, benzocaine, tetracaine, dibucaine, mepivacine, bupivacaine, etidocaine, prilocaine, ropivacaine, proparacaine, chloroprocaine, and lignocaine.

21. The composition as claimed in claim 1, wherein said first ingredient is an anti-histamine selected from the group consisting of diphenhydramine, carbinoxamine, clemastine, dimenhydrinate, pryilamine, tripelennamine, chlorpheniramine, brompheniramine, hydroxyzine, cyclizine, meclizine, chlorcyclizine, promethazine, doxylamine, loratadine, and terfenadine.

22. The composition as claimed in claim 1, wherein said first ingredient is diphenhydramine.

23. The composition as claimed in claim 1, wherein said first ingredient is present in an amount of from 0.01 to 40 percent by weight, based on the total weight of the composition.

24. A method of enhancing the effect of a composition comprising a first ingredient selected from the group consisting of anti-psoriatic agents, anti-dermatitis agents, anti-inflammatory agents other than topical corticosterioids, antihistamines, anti-pruritic agents and local anesthetics, in a topically acceptable vehicle for the topical administration to a person in need thereof, comprising combining with said composition an enhancing amount of at least one second ingredient selected from the group consisting of hydroxycarboxylic acids, lactones and salts thereof and related ketocarboxylic acids, esters, and salts thereof.

25. The method as claimed in claim 24, wherein said second ingredient is selected from the group consisting of a hydroxymonocarboxylic acid, a hydroxydicarboxylic acid or a related compound;

said hydroxymonocarboxylic acid being at least one member selected from the group having the following chemical structure:

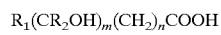

wherein $R_1$, $R_2$=H, alkyl, arakyl or aryl group of saturated or unsaturated, straight or branched chain having 1 to 25 carbon atoms, or cyclic form, m=1, 2, 3, 4, 5, 6, 7, 8 or 9 n=0 or a numerical number up to 23 present as a free acid, lactone or salt form, and as optically active or inactive isomer such as D, L, and DL forms; the hydrogen atom attached to the carbon atom may be substituted by F, Cl, Br, I, or S atom or a lower alkyl or alkoxy saturated or unsaturated radical, having 1 to 9 carbon atoms;

said hydroxydicarboxylic acid being at least one member selected from the group having the following chemical structure:

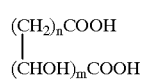

wherein m=1, 2, 3, 4, 5, 6, 7, 8, or 9 n=0 or a numerical number up to 23 present as free acid, lactone or salt form, and as optically active or inactive D, L, and meso isomer; hydrogen atom attached to the carbon atom may be substituted by F, Cl, Br, I, or S atom or a lower alkyl or alkoxy saturated or unsaturated radical, having 1 to 9 carbon atoms; and said related compound being at least one member selected from the group having the following chemical structure:

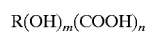

wherein

R=H, alkyl, aralkyl, or aryl group of saturated or unsaturated straight or branched chain, having 1 to 25 carbon atoms, or cyclic form, m and n=1, 2, 3, 4, 5, 6, 7, 8 or 9 present as free acid, lactone or salt form, and as optically active or inactive D, L, and meso isomer; hydrogen atom attached to the carbon atom maybe substituted by F, Cl, Br, I, or S atom or a lower alkyl or alkoxy saturated or unsaturated radical, having 1 to 9 carbon atoms.

26. The method as claimed in claim 24, wherein said second ingredient is selected from the group consisting of 2-hydroxyacetic acid (glycolic acid), 2-hydroxypropanoic acid (lactic acid), 2-methyl 2-hydroxypropanoic acid (methyllactic acid), phenyl 2-hydroxyacetic acid (mandelic acid), diphenyl 2-hydroxyacetic acid (benzilic acid), citric acid, pyruvic acid, ethyl pyruvate, methyl pyruvate, malic acid, tartaric acid, gluconic acid, gluconolactone, ribonic acid, ribonolactone, 4-hydroxymandelic acid, quinic acid, galactonic acid, galactonolactone, gulonic acid, gulonolactone, galacturonic acid, and galacturonolaction.

27. The method as claimed in claim 24, wherein said second ingredient is selected from the group consisting of phenyl 2-methyl 2-hydroxyacetic acid (atrolactic acid), 3-phenyl 2-hydroxypropanoic acid (phenyllactic acid), propyl pyruvate, isopropyl pyruvate, tropic acid, saccharic acid, trethocanic acid, pantoic acid, pantoyllactone, mucic acid, isocitric acid, citramalic acid, agaricic acid, aleuritic acid, erythronic acid, erythronolactone, and ascorbic acid.

28. The method as claimed in claim 24, wherein said second ingredient is a hydroxycarboxylic acid.

29. The method as claimed in claim 24, wherein said second ingredient is glycolic acid.

30. The method as claimed in claim 24, wherein said second ingredient is lactic acid.

31. The method as claimed in claim 24, wherein said second ingredient is citric acid.

32. The method as claimed in claim 24, wherein said second ingredient is 2-methyl 2-hydroxypropanoic acid.

33. The method as claimed in claim 24, wherein said second ingredient is gluconic acid or gluconolactone.

34. The method as claimed in claim 24, wherein said second ingredient is ribonic acid or ribonolactone.

35. The method as claimed in claim 24, wherein said second ingredient is mandelic acid or 4-hydroxymandelic acid.

36. The method as claimed in claim 24 wherein said second ingredient is present as a salt with an organic base or an inorganic alkali.

37. The method as claimed in claim 24, wherein said first ingredient is selected from the group consisting of coal tar, anthralin, lidocaine, sulfur, selenium sulfide, zinc pyrithione, crotamiton, cromolin, procaine, and retinoids.

38. The method as claimed in claim 24, wherein said first ingredient is coal tar.

39. The method as claimed in claim 24, wherein said first ingredient is an anti-psoriatic agent selected from the group consisting of coal tar, anthralin, retinoids, sulfur, selenium sulfide and zinc pyrithione.

40. The method as claimed in claim 24, wherein said first ingredient is an anti-psoriatic agent selected from the group consisting of retinoic acid, 13-cis-retinoic acid, retinyl acetate, retinyl palmitate, retinol, and tazarotene.

41. The method as claimed in claim 39, wherein said first ingredient is anthralin.

42. The method as claimed in claim 24, wherein said first ingredient is an anti-pruritic agent selected from the group consisting of menthol, camphor, phenol, calamine, crotamiton, and doxepin.

43. The method as claimed in claim 24, wherein said first ingredient is a local anesthetic selected from the group consisting of pramoxine, procaine, benzocaine, tetracaine, dibucaine, mepivacine, bupivacaine, etidocaine, prilocaine, ropivacaine, proparacaine, chloroprocaine, and lignocaine.

44. The method as claimed in claim 24, wherein said first ingredient is an anti-histamine selected from the group consisting of diphenhydramine, carbinoxamine, clemastine, dimenhydrinate, pryilamine, tripelennamine, chlorpheniramine, brompheniramine, hydroxyzine, cyclizine, meclizine, chlorcyclizine, promethazine, doxylamine, loratadine, and terfenadine.

45. The method as claimed in claim 24, wherein said first ingredient is diphenhydramine.

46. The method as claimed in claim 22, wherein said first ingredient is present in an amount of from 0.01 to 40 percent by weight, based on the total weight of the composition.

47. A method for topically treating skin conditions or disorders comprising topically applying a composition to said skin, said composition being prepared by:

combining, simultaneously or in any order, a first ingredient selected from the group consisting of anti-psoriatic agents, anti-dermatitis agents, anti-inflammatory agents other than topical corticosteriods, antihistamines, anti-pruritic agents and local anesthetics, with at least one second ingredient;

said second ingredient comprising a composition consisting essentially of an enhancing amount of at least one member selected from the group consisting of hydroxycarboxylic acids, lactones and salts thereof and related ketocarboxylic acids, esters, and salts thereof.

48. The method as claimed in claim 47, wherein said second ingredient is selected from the group consisting of a hydroxymonocarboxylic acid, a hydroxydicarboxylic acid or a related compound;

said hydroxymonocarboxylic acid being at least one member selected from the group having the following chemical structure:

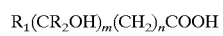

wherein $R_1$, $R_2$=H, alkyl, arakyl or aryl group of saturated or unsaturated, straight or branched chain having 1 to 25 carbon atoms, or cyclic form, m=1, 2, 3, 4, 5, 6, 7, 8 or 9 n=0 or a numerical number up to 23 present as a free acid, lactone or salt form, and as optically active or inactive isomer such as D, L, and DL forms; the hydrogen atom attached to the carbon atom may be substituted by F, Cl, Br, I, or S atom or a lower alkyl or alkoxy saturated or unsaturated radical, having 1 to 9 carbon atoms;

said hydroxydicarboxylic acid being at least one member selected from the group having the following chemical structure:

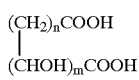

wherein m=1, 2, 3, 4, 5, 6, 7, 8, or 9 n=0 or a numerical number up to 23 present as free acid, lactone or salt form, and as optically active or inactive D, L, and meso isomer; hydrogen atom attached to the carbon atom may be substituted by F, Cl, Br, I, or S atom or a lower alkyl or alkoxy saturated or unsaturated radical, having 1 to 9 carbon atoms; and said related compound being at least one member selected from the group having the following chemical structure:

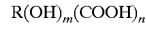

wherein

R=H, alkyl, aralkyl, or aryl group of saturated or unsaturated straight or branched chain, having 1 to 5 carbon atoms, or cyclic form, m and n=1, 2, 3, 4, 5, 6, 7, 8 or 9 present as free acid, lactone or salt form, and as optically active or inactive D, L, and meso isomer; hydrogen atom attached to the carbon atom maybe substituted by F, Cl, Br, I, or S atom or a lower alkyl or alkoxy saturated or unsaturated radical, having 1 to 9 carbon atoms.

49. The method as claimed in claim 24, wherein said second ingredient is selected from the group consisting of 2-hydroxyacetic acid (glycolic acid), 2-hydroxypropanoic acid (lactic acid), 2-methyl 2-hydroxypropanoic acid (methyllactic acid), phenyl 2-hydroxyacetic acid (mandelic acid), diphenyl 2-hydroxyacetic acid (benzilic acid), citric acid, pyruvic acid, ethyl pyruvate, methyl pyruvate, malic acid, tartaric acid, gluconic acid, gluconolactone, ribonic acid, ribonolactone, 4-hydroxymandelic acid, quinic acid, galactonic acid, galactonolactone, gulonic acid, gulonolactone, galacturonic acid, and galacturonolaction.

50. The method as claimed in claim 47, wherein said second ingredient is selected from the group consisting of phenyl 2-methyl 2-hydroxyacetic acid (atrolactic acid), 3-phenyl 2-hydroxypropanoic acid (phenyllactic acid), propyl pyruvate, isopropyl pyruvate, tropic acid, saccharic acid, trethocanic acid, pantoic acid, pantoyllactone, mucic acid, isocitric acid, citramalic acid, agaricic acid, aleuritic acid, erythronic acid, erythronolactone, and ascorbic acid.

51. The method as claimed in claim 47, wherein said second ingredient is a hydroxycarboxylic acid.

52. The method as claimed in claim 47, wherein said second ingredient is glycolic acid.

53. The method as claimed in claim 47, wherein said second ingredient is lactic acid.

54. The method as claimed in claim 47, wherein said second ingredient is citric acid.

55. The method as claimed in claim 47, wherein said second ingredient is 2-methyl 2-hydroxypropanoic acid.

56. The method as claimed in claim 47, wherein said second ingredient is gluconic acid or gluconolactone.

57. The method as claimed in claim 47, wherein said second ingredient is ribonic acid or ribonolactone.

58. The method as claimed in claim 47, wherein said second ingredient is mandelic acid or 4-hydroxymandelic acid.

59. The method as claimed in claim 47 wherein said second ingredient is present as a salt with an organic base or an inorganic alkali.

60. The method as claimed in claim 47, wherein said first ingredient is selected from the group consisting of coal tar, anthralin, lidocaine, sulfur, selenium sulfide, zinc pyrithione, crotamiton, cromolin, procaine, and retinoids.

61. The method as claimed in claim 47, wherein said first ingredient is coal tar.

62. The method as claimed in claim 47, wherein said first ingredient is an anti-psoriatic agent selected from the group consisting of coal tar, anthralin, retinoids, sulfur, selenium sulfide and zinc pyrithione.

63. The method as claimed in claim 47, wherein said first ingredient is an anti-psoriatic agent selected from the group consisting of retinoic acid, 13-cis-retinoic acid, retinyl acetate, retinyl palmitate, retinol, and tazarotene.

64. The method as claimed in claim 47, wherein said skin condition or disorder is psoriasis and said first ingredient is anthralin.

65. The method as claimed in claim 47, wherein said first ingredient is an anti-pruritic agent selected from the group consisting of menthol, camphor, phenol, calamine, crotamiton, and doxepin.

66. The method as claimed in claim 47, wherein said first ingredient is a local anesthetic selected from the group consisting of pramoxine, procaine, benzocaine, tetracaine, dibucaine, mepivacine, bupivacaine, etidocaine, prilocaine, ropivacaine, proparacaine, chloroprocaine, and lignocaine.

67. The method as claimed in claim 47, wherein said first ingredient is an anti-histamine selected from the group consisting of diphenhydramine, carbinoxamine, clemastine, dimenhydrinate, pryilamine, tripelennamine, chlorpheniramine, brompheniramine, hydroxyzine, cyclizine, meclizine, chlorcyclizine, promethazine, doxylamine, loratadine, and terfenadine.

68. The method as claimed in claim 47, wherein said first ingredient is diphenhydramine.

69. The method as claimed in claim 47, wherein said first ingredient is present in an amount of from 0.01 to 40 percent by weight, based on the total weight of the composition.

* * * * *